United States Patent [19]

Plath et al.

[11] Patent Number: 4,521,604
[45] Date of Patent: Jun. 4, 1985

[54] HETEROCYCLIC DIHALOACETAMIDES, AND HERBICIDES WHICH CONTAIN ACETANILIDES AS HERBICIDAL ACTIVE INGREDIENTS AND THE DIHALOACETAMIDES AS ANTAGONISTIC AGENTS

[75] Inventors: Peter Plath, Ludwigshafen; Wolfgang Rohr, Wachenheim; Volker Schwendemann, Wiesenbach; Bruno Wuerzer, Otterstadt, all of Fed. Rep. of Germany

[73] Assignee: BASF Aktiengesellschaft, Fed. Rep. of Germany

[21] Appl. No.: 376,744

[22] Filed: May 10, 1982

[30] Foreign Application Priority Data

May 14, 1981 [DE] Fed. Rep. of Germany ....... 3119077

[51] Int. Cl.³ .................... A01N 9/02; C07D 233/32; C07D 241/08
[52] U.S. Cl. ...................... 548/301; 71/92; 544/231; 544/354; 544/384; 548/302
[58] Field of Search ............ 544/384, 354, 231; 548/301–302

[56] References Cited

U.S. PATENT DOCUMENTS

| 4,021,224 | 5/1977 | Pallos et al. | 71/88 |
| 4,110,327 | 8/1978 | Saikawa et al. | 544/384 |
| 4,167,512 | 9/1979 | Lai et al. | 544/384 |
| 4,190,571 | 2/1980 | Lai et al. | 544/384 |

FOREIGN PATENT DOCUMENTS

| 45-8422 | 3/1970 | Japan | 544/354 |
| B1403264 | 8/1975 | United Kingdom | |

Primary Examiner—Glennon H. Hollrah
Assistant Examiner—James H. Turnipseed
Attorney, Agent, or Firm—Keil & Weinkauf

[57] ABSTRACT

Heterocyclic dihaloacetamides of the formula

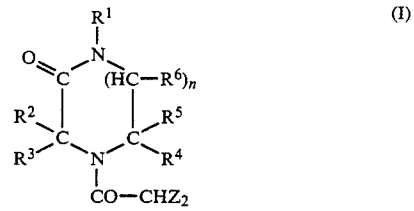

where $R^1$ to $R^6$, Z and n have the meanings given in the description, are antagonistic agents which increase the toleration of herbicidal acetanilides by crops.

2 Claims, No Drawings

HETEROCYCLIC DIHALOACETAMIDES, AND HERBICIDES WHICH CONTAIN ACETANILIDES AS HERBICIDAL ACTIVE INGREDIENTS AND THE DIHALOACETAMIDES AS ANTAGONISTIC AGENTS

The present invention relates to heterocyclic dihaloacetamides, and herbicides which contain acetanilides as herbicidal active ingredients and the dihaloacetamides as antagonistic agents.

Acetanilides of the formula

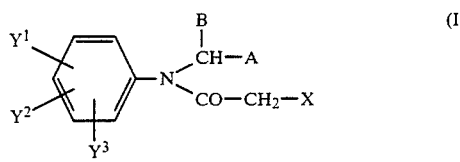

where $Y^1$ is hydrogen or straight-chain or branched alkyl or alkoxy of not more than 5 carbon atoms and $Y^2$ and $Y^3$ are hydrogen, halogen or straight-chain or branched alkyl or alkoxy of not more than 5 carbon atoms, or $Y^1$ and $Y^2$ together are alkylene of not more than 6 carbon atoms which is linked in the ortho-position and is unsubstituted or substituted by straight-chain or branched alkyl of not more than 4 carbon atoms, X is chlorine or bromine, A is alkoxy or alkoxyalkyl of not more than 4 carbon atoms, or is azolyl, which may be monosubstituted or polysubstituted by halogen or phenyl, or by alkyl, alkoxy, alkylthio or perfluoroalkyl, each of not more than 4 carbon atoms, or by cyano, carboxyl or alkoxycarbonyl where alkoxy is of not more than 4 carbon atoms, and A can also be a salt of an azolyl radical, which contains 2 or 3 nitrogen atoms, and B is hydrogen or methyl, are excellent herbicides, but cause damage to crops such as Indian corn or other crops of the Gramineae family.

It is an object of the present invention to provide antagonists which counterbalance this intolerance of herbicidal acetanilides by certain crops.

German Laid-Open Applications DOS No. 2,218,097 and DOS No. 2,245,471 disclose herbicides which, in addition to herbicidal active ingredients, contain dichloroacetamides as antagonistic compounds. The dichloroacetamides disclosed in German Laid-Open Application DOS No. 2,218,097 are chiefly used for reducing undesirable crop damage caused by thiolcarbamates, while German Laid-Open Application DOS No. 2,245,471 also discloses herbicides which contain dichloroacetamides and chloroacetanilides, e.g. 2-chloro-2′,6′-diethyl-N-butoxymethylacetanilide or 2-chloro-2′,6′-diethyl-N-methoxymethylacetanilide.

We have found that the above object is achieved by heterocyclic dihaloacetamides of the formula

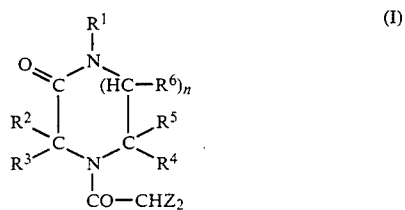

where $R^1$ is hydrogen or alkyl of 1 to 4 carbon atoms, $R^2$ is hydrogen or methyl, $R^3$ is hydrogen or alkyl of 1 to 3 carbon atoms, $R^4$ is hydrogen, alkyl of 1 to 4 carbon atoms or cyclohexyl, $R^5$ is hydrogen or methyl, $R^6$ is hydrogen or methyl, Z is chlorine or bromine and n is 0 or 1, or where $R^2$ together with $R^3$ is pentamethylene, or where $R^4$ together with $R^5$ is tetramethylene or pentamethylene, if n is 0, or where $R^5$ together with $R^6$ is tetramethylene, if n is 1, which are particularly suitable for increasing the toleration of herbicidal acetanilides of the formula II by plants. Herbicides containing an acetanilide of the formula II and a heterocyclic dihaloacetamide of the formula I can be used both on Indian corn and on other cereal crops. The good herbicidal effect of the acetanilides is retained, while damage to the crops is entirely or substantially avoided.

Suitable antagonists include heterocyclic dihaloacetamides of the formula I where n is 0 or 1, i.e. both 1-dihaloacetyl-imidazolidin-4-ones and 1-dihaloacetylpiperazin-3-ones. In formula I, $R^1$ is hydrogen or alkyl of 1 to 4 carbon atoms, e.g. methyl, ethyl, isopropyl or isobutyl, $R^2$ is hydrogen or methyl, $R^3$ is hydrogen or alkyl of 1 to 3 carbon atoms, e.g. methyl, ethyl or isopropyl, $R^4$ is hydrogen, alkyl of 1 to 4 carbon atoms, e.g. methyl, ethyl, isopropyl or tert.-butyl, or cyclohexyl, and $R^5$ and $R^6$ are each hydrogen or methyl. $R^2$ together with $R^3$ can also be pentamethylene, and in addition, $R^4$ together with $R^5$ can be tetramethylene or pentamethylene, if n is 0, or $R^5$ together with $R^6$ can be tetramethylene, if n is 1.

Examples of antagonistic dihaloacetamides of the formula I are 1-dichloroacetyl-2-spiro-cyclohexyl-4-oxo-imidazolidine, 1-dichloroacetyl-2-isopropyl-4-oxo-imidazolidine, 1-dichloroacetyl-2,5-dimethyl-2-isopropyl-4-oxo- imidazolidine, 1-dichloroacetyl-2-isopropyl-4-oxo-5-methyl-imidazolidine, 1-dichloroacetyl-2-spiro-cyclopentyl-4-oxo-imidazolidine, 1-dichloroacetyl-2,3-diisopropyl-4-oxo-imidazolidine, 1-dichloroacetyl-2-isopropyl-4-oxo-5,5-dimethyl-imidazolidine, 1-dichloroacetyl-2-tert.-butyl-4-oxo-imidazolidine, 1-dichloroacetyl-2-cyclohexyl-4-oxo-imidazolidine, 1-dichloroacetyl-2-isopropyl-3-methyl-4-oxo-imidazolidine, 1-dichloroacetyl-2-tert.-butyl-3-methyl-4-oxo-imidazolidine, 1-dichloroacetyl-2-cyclohexyl-4-oxo-imidazolidine, 1-dichloroacetyl-2-cyclohexyl-3-methyl-4-oxo-imidazolidine, 1-dibromoacetyl-2-tert.-butyl-3-methyl-4-oxo-imidazolidine, 1-dibromoacetyl-2-cyclohexyl-4-oxo-imidazolidine, 1-dichloroacetyl-3-oxo-piperazine, 1-dichloroacetyl-2-methyl-3-oxo-piperazine, 1-dichloroacetyl-2,5-dimethyl-3-oxo-piperazine, 1-dichloroacetyl-2,2-dimethyl-3-oxo-piperazine, 1-dichloroacetyl-2,5,6-trimethyl-3-oxo-piperazine, 1-dichloroacetyl-2-methyl-3-oxo-5,6-tetramethylene-piperazine, 1-dichloroacetyl-2-ethyl-3-oxo-piperazine, 1-dichloroacetyl-2-isopropyl-3-oxo-piperzine, 1-dichloroacetyl-2-spirocyclohexyl-2-oxo-piperazine, 1-dichloroacetyl-2-spirocyclohexyl-3-oxo-5,6-tetramethylene-piperazine, 1-dibromoacetyl-2,2-dimethyl-3-oxo-piperazine and 1-dibromoacetyl-2-methyl-3-oxo-piperazine.

Heterocyclic dichloroacetamides of the formula I can be obtained by reacting an amine of the formula

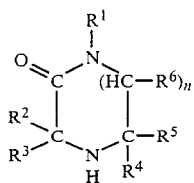

where $R^1$ to $R^6$ and n have the above meanings, with a dihaloacetyl chloride of the formula $Z_2CH-COCl$, where Z is chlorine or bromine, in the presence of a hydrogen halide acceptor and a solvent, at from 0° to 30° C.

Suitable solvents are anhydrous solvents, e.g. hydrocarbons or halohydrocarbons, such as toluene, the xylenes, chlorobenzene, methylene chloride and ethylene chloride, ethers, such as diethyl ether, methyl tert.-butyl ether, tetrahydrofuran or 1,4-dioxane, and nitriles, such as acetonitrile, and two-phase systems, e.g. water and toluene, or water and methylene chloride.

Suitable hydrogen halide acceptors are alkali metal carbonates and bicarbonates, aqueous solutions of alkali metal hydroxides, and trialkylamines, N,N-dialkylanilines, e.g. N,N-dimethylaniline, and pyridine bases. Advantageously, 1 mole of the amine of the formula III is reacted with 1 to 1.2 moles of dihaloacetyl chloride. 1–1.2 moles of hydrogen halide acceptor are added per mole of dihaloacetyl chloride.

Imidazolidin-4-ones of the formula III are prepared by reacting a ketone or aldehyde with a nitrile or amide of an α-aminoacid (J. Chem. Soc. (1951), 3479), or by converting an α-aminoacid ester into a Schiff base and then reacting the base with ammonia or a primary amine (Rec. Trav. Chim. 111 (1971), 284).

Piperazinones of the formula III are obtained, for example, by reacting a cyanohydrin with an aliphatic 1,2-diamine (U.S. Pat. No. 2,700,668).

Preparation of the amines of the formula III 1. 137 g of cyclohexanone were added to a suspension of 77 g (0.69 mole) of glycinamide hydrochloride in 300 ml of toluene, and a mixture of 120 ml of methanol and 125.5 g of 30% strength NaOCH₃ solution (0.7 mole) was then added dropwise at 25° C. The mixture was refluxed for 4 hours and cooled to 5° C., the precipitated NaCl was filtered off with suction and the filtrate was evaporated. Trituration of the residue with naphtha gave 44 g (41% of theory) of 2-spiro-cyclohexyl-4-oxo-imidazolidine or melting point 118°–119° C.

2. 279 g (2 moles) of methyl alanate hydrochloride were dissolved in 100 ml of water, and 216 g (3 moles) of isobutyraldehyde were rapidly added. 242 g (2.4 moles) of triethylamine were then added dropwise at from 10 to 15° C., and the mixture was stirred for 16 hours and extracted with 250 ml of methyl tert.-butyl ether. The organic phase was dried, and concentrated under reduced pressure to give 281 g (89% of theory) of an oil of the formula (CH₃)₂CH—CH=N—CH(CH₃)—COOCH₃

62.8 g (0.4 mole) of this Schiff base were dissolved in 200 ml of methanol, and gaseous methylamine was added at 25° C. until the mixture was saturated. The mixture was stirred for 16 hours and concentrated under reduced pressure to give 58 g (93% of theory) of 3,5-dimethyl-2-isopropyl-4-oxo-imidazolidine as an oil.

3. N-(2-Methyl-propylidene)-glycine ethyl ester of boiling point 53°–56° C./0.1 mbar was obtained in 90% yield from glycine methyl ester hydrochloride and isobutyraldehyde in a reaction similar to that described under 2. The reaction of this Schiff base with gaseous ammonia in methanol gave an 80% yield of 2-isopropyl-4-oxo-imidazolidine as an oil.

4. 138.5 g (1.95 moles) of acetaldehyde cyanohydrin were added dropwise to a solution of 176 g (2 moles) of 2,3-diaminobutane in 250 ml of water, with cooling at 25° C. The mixture was then heated at the boil for 8 hours, until no more ammonia was split off. The reaction mixture was then distilled under reduced pressure to give 200 g (72% of theory) of 2,5,6-trimethyl-3-oxo-piperazine of boiling point 123° C./0.5 mbar.

5. 2-Methyl-3-oxo-5,6-tetramethylene-piperazine of melting point 177°–178° C. was obtained from 1,2-diaminocyclohexane and acetaldehyde cyanohydrin by a reaction similar to that described under 4.

6. 2,2-Dimethyl-3-oxo-piperazine of melting point 133°–135° C. was obtained from ethylenediamine and acetone cyanohydrin by a reaction similar to that described under 4.

Preparation of the heterocyclic dihaloacetamides of the formula I

I. 45 g (0.35 mole) of 2-isopropyl-4-oxo-imidazolidine (Example 3) were dissolved in 250 ml of methyl tert.-butyl ether, 17.2 g (0.43 mole) of sodium hydroxide in 20 ml of water were added, and 57 g (0.39 mole) of dichloroacetyl chloride were then added dropwise at from 10° to 15° C. The mixture was stirred for 10 hours and the solid precipitate was filtered off with suction, washed with water and dried under reduced pressure to give 41 g (49% theory) of 1-dichloroacetyl-2-isopropyl-4-oxoimidazolidine of melting point 172°–173° C.

II. A solution of 8 g (0.2 mole) of sodium hydroxide in 15 ml of water was added to a solution of 20 g (0.18 mole) of 2-methyl-piperazin-3-one in 150 ml of methylene chloride. 26.6 g (0.18 mole) of dichloroacetyl chloride were then added dropwise at from 10° to 15° C. The mixture was stirred at 25° C. for 10 hours and the precipitated crude product was filtered off with suction, washed with water and recrystallized from a 2:1 mixture of isopropanol and H₂O to give 14.4 g (36% theory) of 1-dichloroacetyl-2-methyl-3-oxo-piperazine of melting point 167°–168° C.

The dihaloacetamides listed in Tables 1 and 2 may be obtained in a similar manner.

TABLE 1

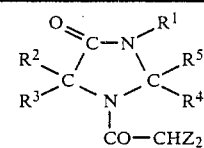

| No. | $R^1$ | $R^2$ | $R^3$ | $R^4$ | $R^5$ | Z | Melting point [°C.] |
|---|---|---|---|---|---|---|---|
| 1 | H | H | H | i-C₃H₇ | H | Cl | 172–173 |
| 2 | H | H | CH₃ | i-C₃H₇ | H | Cl | 198–199 |
| 3 | CH₃ | H | CH₃ | i-C₃H₇ | H | Cl | 114–115 |
| 4 | H | H | H | —(CH₂)₅— | | Cl | 218 |
| 5 | i-C₃H₇ | H | H | i-C₃H₇ | H | Cl | |
| 6 | H | CH₃ | CH₃ | i-C₃H₇ | H | Cl | |
| 7 | H | H | H | tert.-C₄H₉ | H | Cl | 174–176 |

TABLE 1-continued

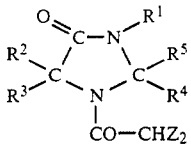

| No. | $R^1$ | $R^2$ | $R^3$ | $R^4$ | $R^5$ | Z | Melting point [°C.] |
|---|---|---|---|---|---|---|---|
| 8 | H | H | H | $C_6H_{11}$ | H | Cl | |
| 9 | $CH_3$ | H | H | $i$-$C_3H_7$ | H | Cl | |
| 10 | $CH_3$ | H | H | tert.-$C_4H_9$ | H | Cl | 112 |
| 11 | H | H | H | $C_6H_{11}$ | H | Cl | 209 |
| 12 | $CH_3$ | H | H | $C_6H_{11}$ | H | Cl | 152 |
| 13 | H | H | H | $C_6H_{11}$ | H | Br | 202 |
| 14 | $CH_3$ | H | H | $C_6H_{11}$ | H | Br | |
| 15 | n-$C_4H_9$ | H | H | tert.-$C_4H_9$ | H | Cl | |
| 16 | i-$C_3H_7$ | H | H | tert.-$C_4H_9$ | H | Cl | |
| 17 | H | $CH_3$ | $CH_3$ | i-$C_3H_7$ | H | Cl | |
| 18 | $CH_3$ | $CH_3$ | $CH_3$ | i-$C_3H_7$ | H | Cl | |
| 19 | $CH_3$ | H | H | tert.-$C_4H_9$ | H | Br | 141 |

TABLE 2

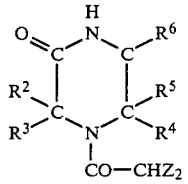

| No. | $R^2$ | $R^3$ | $R^4$ | $R^5$ | $R^6$ | Z | Melting point [°C.] |
|---|---|---|---|---|---|---|---|
| 20 | H | H | H | H | H | Cl | |
| 21 | H | $CH_3$ | H | H | H | Cl | 167–168 |
| 22 | $CH_3$ | H | H | H | $CH_3$ | Cl | 153–155 |
| 23 | $CH_3$ | $CH_3$ | H | H | H | Cl | 196–197 |
| 24 | H | $CH_3$ | $CH_3$ | H | $CH_3$ | Cl | 145–147 |
| 25 | $CH_3$ | H | H | —$(CH_2)_4$— | | Cl | 247–248 |
| 26 | H | $C_2H_5$ | H | H | H | Cl | |
| 27 | H | i-$C_3H_7$ | H | H | H | Cl | |
| 28 | —$(CH_2)_5$ | | H | H | H | Cl | |
| 29 | —$(CH_2H_5$— | H | —$(CH_2)_4$ | | | Cl | |
| 30 | H | $CH_3$ | H | H | H | Br | |
| 31 | H | $CH_3$ | $CH_3$ | H | H | Br | |
| 32 | $CH_3$ | $CH_3$ | H | H | H | Br | 135 (decomposition) |

The dihaloacetamides of the formula I can be used to improve the toleration by crops of those acetanilides of the formula II where $Y^1$ is hydrogen, alkyl of not more than 5 carbon atoms, e.g. methyl, ethyl, n-propyl, i-propyl, n-butyl, sec.-butyl, i-butyl, tert.-butyl or normal or branched pentyl, or alkoxy of not more than 5 carbon atoms, e.g. methoxy, ethoxy, propoxy, butoxy or pentyloxy, and $Y^2$ and $Y^3$ are hydrogen, halogen, e.g. fluorine, chlorine, bromine or iodine, alkyl of not more than 5 carbon atoms, e.g. methyl, ethyl, n-propyl, i-propyl, n-butyl, sec.-butyl, i-butyl, tert.-butyl or normal or branched pentyl, or alkoxy of not more than 5 carbon atoms, e.g. methoxy, ethoxy, propoxy, butoxy or pentyloxy, or $Y^1$ together with $Y^2$ is alkylene of not more than 6 carbon atoms, which is linked in the ortho-position and is unsubstituted or substituted by alkyl of not more than 4 carbon atoms, such as ethylene, trimethylene, tetramethylene, 1-methyl-trimethylene, 1,1-dimethyltrimethylene or 1,1-dimethyl-tetramethylene, X is chlorine or bromine, preferably chlorine, A is azolyl, e.g. pyrrolyl, pyrazolyl, imidazolyl, 1,2,4-triazolyl, 1,2,3-triazolyl or tetrazolyl, which can be monosubstituted or polysubstituted by halogen or phenyl, or by alkyl, alkoxy, alkylthio or perfluoroalkyl, each of not more than 4 carbon atoms, or by cyano, carboxyl or alkoxycarbonyl, where alkoxy is of not more than 4 carbon atoms, or A is alkoxy or alkoxyalkyl of not more than 4 carbon atoms, e.g. methoxy, ethoxy, n-butoxy, methoxymethyl, 2-methoxymethyl or ethoxymethyl, and B is hydrogen or methyl.

Moreover, if the azolyl radical A contains 2 or 3 nitrogen atoms, it can also be bonded in the form of a salt to one of the conventional strong inorganic or organic acids, such as hydrochloric acid, nitric acid, sulfuric acid, trichloroacetic acid, methanesulfonic acid, perfluorohexanesulfonic acid or dodecylbenzenesulfonic acid.

Preferred acetanilides of the formula II are those which carry methyl or ethyl in the 2- and 6-positions of the phenyl ring and hydrogen or methyl in the 3-position. X is preferably chlorine, while A is, in particular, azolyl, e.g. pyrazolyl, 3,5-dimethylpyrazolyl, 2-methylpyrazol-5-yl, 1,2,4-triazolyl or 4,5-dichloroimidazolyl, or ethoxy, n-butoxy or methoxymethyl, and B is hydrogen or methyl.

In particular, the herbicides according to the invention contain the following acetanilides: 2-chloro-2',6-dimethyl-N-(pyrazol-1-yl-methyl)-acetanilide, 2-chloro-2'-methyl-6'-ethyl-N-(pyrazol-1-yl-methyl)-acetanilde, 2-chloro-2',6'-dmethyl-N-(3,5-dimethyl-pyrazol-1-yl-methyl)-acetanilide, 2-chloro-2',6'-dimethyl-N-(1,2,4-triazol-1-yl-methyl)-acetanilide, 2-chloro-2',3',6'-trimethyl-N-(pyrazol-1-yl-methyl)-acetanilide, 2-chloro-2'-methyl-6'-ethyl-N-(3,5-dimethyl-pyrazol-1-yl-methyl)-acetanilide, 2-chloro-2',6'-diethyl-N-(3,5-dimethylpyrazol-1-yl-methyl)-acetanilide, 2-chloro-2',3',6'-trimethyl-N-(3,5-dimethyl-pyrazol-1-yl-methyl)-acetanilide, 2-chloro-2',6'-diethyl-N-(pyrazol-1-yl-methyl)-acetanilide, 2-chloro-2',6'-dimethyl-N-(4,5-dichloroimidazol-1yl-methyl)-acetanilide, 2-chloro-2'-methyl-6'-ethyl-N-(4,5-dichloroimidazol-1-yl-methyl)-acetanilide, 2-chloro-2',6'-diethyl-N-(4,5-dichloroimidazol-1-yl-methyl)-acetanilide, 2-chloro-2'-methyl-6'-ethyl-N-(1,2,4-triazol-1-yl-methyl)-acetanilide, 2-chloro-2',6'-diethyl-N-(1,2,4-triazol-1-yl-methyl)-acetanilide, 2-chloro-2',3',6'-trimethyl-N-(1,2,4-triazol-1-yl-methyl)-acetanilide, 2-chloro-2',6'-dimethyl-N-(2-methoxyethyl)-acetanilide, 2-chloro-2'-methyl-6'-ethyl-N-ethoxymethyl-acetanilide, 2-chloro-2',6'-diethyl-N-(n-butoxymethyl)-acetanilide, 2-chloro-2'-ethyl-6'-methyl-N-(1-methyl-2-methoxy-ethyl)-acetanilide and 2- chloro-2',6'-dimethyl-N-[(2-methylpyrazol-5-yl))-methyl]acetanilide.

German Laid-Open Applications DOS No. 2,648,008, DOS No. 2,744,396, DOS No. 2,305,495, DOS No. 2,328,340 and DOS No. 2,842,315 and U.S. Pat. No. 3,547,620 disclose the acetanilides of the formula II and their preparation.

Herbicidal active ingredients and antagonistic compounds can be worked into the soil together or separately, before or after sowing. The acetanilides are in most cases applied to the surface of the soil immediately after the seeds have been sown or in the period between sowing and emergence of the young plants. Treatment during emergence is also possible. In all cases, the antagonist can be applied at the same time as the herbicidal active ingredient. Separate application, first of the antagonist and then of the herbicidal active ingredient or vice versa, to the field is also possible as long as the interval between the two applications is not so long that the herbicidal active ingredient has already caused damage to the crop. The active ingredient and antagonist can be formulated separately or together as sprays, in suspendable, emulsifiable or soluble form, or as granules. Treatment of the crop seeds with the antagonist before sowing is also conceivable, in which case the herbicidal active ingredient is applied by itself in a conventional manner.

Different amounts of a given antagonistic compound may be required for the same herbicidal acetanilide, depending on the crop, and the proportions in which the acetanilide and dihaloacetamide are used can vary within wide limits, depending on the structure of the acetanilide and of the dihaloacetamide and on the particular crop. A suitable weight ratio of herbicidal active ingredient to antagonistic compound is from 1:2 to 1:0.01, preferably from 1:0.25 to 1:0.05.

The new herbicidal agents may contain, in addition to acetanilide and dihaloacetamide, further herbicidal or growth-regulating active ingredients having a different chemical structure, the antagonistic effect being retained. They may for instance contain 2-chloro-4-ethylamino-6-isopropylamino-1,3,5-triazine, 2-(2-chloro-4-ethylamino-1,3,5-triazin-6-yl-amino)-2-methyl-propionitrile, N-(1-ethyl-n-propyl)-2,6-dinitro-3,4-dimethylaniline or 1-(4-isopropyl-phenyl)-3,3-dimethylurea as additional herbicidal active ingredients.

The agents according to the invention, or— where applied separately— the herbicidal active ingredients and antidote, are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredients and/or antidote as such or dissolved in an oil or solvent may be homogenized in water by means of wetting or dispersing agents, adherents or emulsifiers. Concentrates which are suitable for dilution with water may be prepared from herbicidal active ingredient and/or antidote, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the herbicidal active ingredients and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contains from 0.1 to 95, and preferably 0.5 to 90%, by weight of herbicidal active ingredient and antidote. Application rates are from 0.2 to 5 kg of active ingredient per hectare. This amount of active ingredient is applied, conjointly or in a separate operation, with such an amount of antidote that the weight ratio of herbicidal active ingredient to antagonistic compound is from 1:2 to 1:0.01, and preferably from 1:0.25 to 1:0.05.

Examples of formulations are given below.

I. 40 parts by weight of a mixture of 4 parts by weight of 2-chloro-2',6'-dimethyl-N-(pyrazol-1-yl-methyl)-acetanilide and 1 part by weight of 1-dichloroacetyl-2-isopropyl-4-oxo-imidazolidine is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt % of active ingredient mixture.

II. 3 parts by weight of a mixture of 1 part by weight of 2-chloro-2'-methyl-6'-ethyl-N-(pyrazol-1-yl-methyl)-acetanilide and 1 part by weight of 1-dichloroacetyl-2,2-dimethyl-3-oxo-piperazine is intimately mixed with 97 parts by weight of particulate kaolin. A dust is obtained containing 3% by weight of the mixture of active ingredients.

III. 30 parts by weight of a mixture of 1 part by weight of 2-chloro-2'methyl-6'-ethyl-N-(1,2,4-triazol-1-yl-methyl)-acetanilide and 2 parts by weight of 1-dichloroacetyl-2,5,6-trimethyl-3-oxo-piperazine is intimately mixed with a mixture consisting of 92 parts by weight of powdered silica gel and 8 parts by weight of paraffin oil which has been sprayed onto the surface of this silica gel. A formulation of the active ingredient mixture is obtained having good adhercene.

IV. 20 parts by weight of a mixture of 8 parts by weight of 2-chloro-2'-methyl-6'-ethyl-N-ethoxymethylacetanilide and 1 part by weight of 1-dichloroacetyl-2-isopropyl-3,5-dimethyl-4-oxo-imidazoline is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 20 parts by weight of a mixture of 10 parts by weight of 2-chloro-2',6'-dimethyl-N-(2-methoxyethyl)-acetanilide and 1 part by weight of 1-dichloroacetyl-2-methyl-3-oxo-5,6-tetramethylene-piperazine is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueus disperson is obtained containing 0.02% by weight of the active ingredient mixture.

The influence of various representatives of herbicides according to the invention on the growth of unwanted and crop plants compared with that of herbicides consisting of the same herbicidal active ingredients and a prior art antagonistic compound of chemically similar structure is demonstrated in the following biological experiments. These experiments show that the tolerance of the herbicidal acetanilides by combined application with the dihaloacetamides is decisively improved and the herbicidal effectiveness retained.

The series of experiments were carried out in the greenhouse.

Plastic boxes 51 cm long, 32 cm wide and 6 cm deep were filled with loamy sand (ph:6 to 7) containing about 1.5 to 3% humus. Indian corn (*Zea mays*) and barley (*Hordeum vulgare*) were sown shallow, in rows, in this substrate. *Echinochloa crus-galli* and *Alopecurus myosuroides* were scattered at random as unwanted plants. The non-sterilized soil also additionally contained viable weed seeds which contributed to the weed population. A field with crop plants growing in it and infested with weeds was thus simulated.

The active ingredients and antagonists were applied separately and in the mixtures given below. They were emulsified or suspended in water as vehicle and the liquor was sprayed through finely distributing nozzles onto the soil surface, either immediately after sowing or prior to emergence of the test plants. In some instances, the agents were also incorporated into the soil before the crop plants were sown. For the seed treatment the seed was powdered with a solid formulation of the active ingredients, or soaked for a certain period of time in a liquid formulation (suspension, emulsion, solution) of the antagonistic compound, dried to such a degree that the seeds no longer stuck to each other, and then sown. Seed coating is also possible. After sowing and treatment, the boxes were sprinkler-irrigated and covered with transparent plastic hoods until the plants emerged. These measures ensured that the plants germinated and took root uniformly. The boxes were set up in the greenhouse at from 15° to 25° C.

These greenhouse experiments were monitored until 3 to 5 Indian corn leaves had developed. No more damage due to the herbicidal agents was to be expected after this stage. In the case of barley, the test period was from 2 to 3 weeks.

The scale for assessing the action of the agents was 0 to 100, 0 denoting normal emergence and development of the plants, with reference to the untreated control, and 100 denoting non-germination or withering of the plants.

As comparative agents, herbicidal agents were used which contained, in addition to he herbicidal acetanilide, N-dichloroacetyl-morpholine (V) (disclosed in German Laid-Open Application DE-OS No. 2,218,097) as antagonistic agent.

TABLE 3

Improvement in the tolerance of 2-chloro-2',6'-dimethyl-N—(pyrazol-1-yl-methyl)-acetanilide (A) by Indian corn, by admixing antagonistic compounds; preemergence treatment in the greenhouse

| Herbicidal active ingredient | Antagonistic compound | Appln. rate [kg/ha] | Test plants and % damage | |
|---|---|---|---|---|
| | | | Zea mays | Echinochloa crus-galli |
| A | — | 1.0 | 64 | 100 |
| A | V | 1.0 + 0.125 | 37 | 100 |
| A | 23 | 1.0 + 0.125 | 8 | 100 |
| | | 1.0 + 0.1 | 8 | 100 |
| | | 1.0 + 0.06 | 12 | 100 |
| A | 21 | 1.0 + 0.25 | 12 | 100 |
| | | 1.0 + 0.1 | 18 | 100 |
| A | 1 | 1.0 + 0.125 | 0 | — |

0 = normal emergence, no damage
100 = non-emergence, or plants withered

TABLE 4

Improvement in the tolerance of 2-chloro-2',6'-dimethyl-N—(pyrazol-1-yl-methyl)-acetanilide (A) by cereals, by admixing an antagonistic compound; preemergence treatment in the greenhouse

| Herbicidal active ingredient | Antagonistic compound | Appln. rate [kg/ha] | Test plants and % damage | |
|---|---|---|---|---|
| | | | Hordeum vulgare | Alopecurus myosuroides |
| A | — | 0.5 | 65 | 90 |
| A | 25 | 0.5 + 0.5 | 15 | 95 |

0 = normal emergence, no damage
100 = non-emergence, or plants withered

TABLE 5

Improvement in the tolerance by Indian corn of 2-chloro-2',6'-dimethyl-N—(pyrazol-1-yl-methyl)-acetanilide (A) by seed treatment

| Herbicidal active ingredient | Antagonistic compound | Appln. rate (a.i. + antagonist kg) | Method | Test plants and % damage | |
|---|---|---|---|---|---|
| | | | | Zea mays | Echinochloa crus-galli |
| A | — | 1.0 | PES* | 68 | 99 |
| A | 23 | 1.0 + 250 g per 100 kg seed | PES as seed treatment | 0 | 100 |
| A | 23 | 1.0 + 50 kg per 100 kg seed | PES as seed treatment | 0 | 100 |

TABLE 5-continued

Improvement in the tolerance by Indian corn of 2-chloro-2',6'-dimethyl-N—(pyrazol-1-yl-methyl)-acetanilide (A) by seed treatment

| Herbicidal active ingredient | Antagonistic compound | Appln. rate (a.i. + antagonist kg) | Method | Test plants and % damage | |
|---|---|---|---|---|---|
| | | | | Zea mays | Echinochloa crus-galli |
| A | 22 | 1.0 + 250 g per 100 kg seed | PES as seed treatment | 10 | 100 |
| A | 22 | 1.0 + 50 g per 100 kg seed | PES as seed treatment | 10 | 100 |

*PES = Preemergence spraying (after sowing of crop and unwanted plants)
The seed was treated with the antagonistic compound, and the herbicidal active ingredient was sprayed after the seed had been sown.

TABLE 6

Improvement in the tolerance by Indian corn of 2-chloro-2',6'-dimethyl-N—(2-methoxyethyl)-acetanilide (B) and 2-chloro-2'-methyl-6'-ethyl-N—(ethoxymethyl)-acetanilide (C); preemergence application in the greenhouse

| Herbicidal active ingredient | Antagonistic compound | Appln. rate [kg/ha] | Damage to crop plant Indian corn in % Zea mays |
|---|---|---|---|
| B | — | 1.0 | 45 |
| B | 23 | 1.0 + 0.25 | 0 |
| | 23 | 1.0 + 0.125 | 5 |
| C | | 2.0 | 32 |
| C | 23 | 2.0 + 0.25 | 5 |

We claim:

1. Heterocyclic dihaloacetamides of the formula

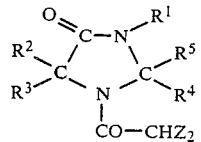

where $R^1$ is hydrogen or alkyl of 1 to 4 carbon atoms, $R^2$ is hydrogen or methyl, $R^3$ is hydrogen or alkyl of 1 to 3 carbon atoms, $R^4$ is hydrogen, alkyl of 1 to 4 carbon atoms or cyclohexyl, $R^5$ is hydrogen or methyl, Z is chlorine or bromine and n is 0, or where $R^2$ together with $R^3$ is pentamethylene, or where $R^4$ together with $R^5$ is tetramethylene or pentamethylene.

2. 1-Dichloroacetyl-2-isopropyl-4-oxo-imidazolidine.

* * * * *